US006342247B1

(12) United States Patent
Ku et al.

(10) Patent No.: US 6,342,247 B1
(45) Date of Patent: Jan. 29, 2002

(54) PHARMACEUTICAL COMPOSITIONS CONTAINING IRBESARTAN

(75) Inventors: Cathy C. Ku, Martinsville; Omar L. Sprockel, Bridgewater; Beth A. Lang, Bedminster; Divvakant S. Desai, Robbinsville, all of NJ (US)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/686,378

(22) Filed: Oct. 11, 2000

Related U.S. Application Data

(63) Continuation of application No. 09/390,868, filed on Sep. 7, 1999, now abandoned, which is a division of application No. 09/081,685, filed on May 20, 1998, now Pat. No. 5,994,348, which is a continuation of application No. 08/642,978, filed on May 6, 1996, now abandoned, which is a continuation-in-part of application No. 08/472,618, filed on Jun. 7, 1995, now abandoned.

(51) Int. Cl.$^7$ ................................................. A61K 9/20
(52) U.S. Cl. .................... 424/465; 424/464; 424/422; 424/400; 514/381; 514/223.5
(58) Field of Search .................. 514/381, 223.5; 424/464, 465

(56) References Cited

U.S. PATENT DOCUMENTS

| | | | |
|---|---|---|---|
| 4,414,198 A | 11/1983 | Michaelson | 424/44 |
| 4,769,236 A | 9/1988 | Panoz et al. | 424/80 |
| 4,793,999 A | 12/1988 | Sheth | 424/451 |
| 4,804,540 A | 2/1989 | Nugent et al. | 424/457 |
| 4,808,413 A | 2/1989 | Joshi et al. | 424/458 |
| 4,898,729 A | 2/1990 | Miller et al. | 424/80 |
| 4,904,699 A | 2/1990 | Bauer | 514/972 |
| 4,910,022 A | 3/1990 | Bavitz et al. | 424/465 |
| 4,952,410 A | 8/1990 | Armah et al. | 424/465 |
| 5,006,344 A | 4/1991 | Jerzewski et al. | 424/465 |
| 5,037,823 A | 8/1991 | Jones et al. | 514/222.8 |
| 5,047,246 A | 9/1991 | Gallian et al. | 424/464 |
| 5,049,394 A | 9/1991 | Howard et al. | 424/490 |
| 5,073,374 A | 12/1991 | McCarty | 424/435 |
| 5,087,454 A | 2/1992 | Duerholz et al. | 424/464 |
| 5,112,616 A | 5/1992 | McCarty | 424/435 |
| 5,155,105 A | 10/1992 | Jones et al. | 514/223.5 |
| 5,270,317 A | 12/1993 | Bernhart et al. | 514/269 |
| 5,288,501 A | 2/1994 | Nurnberg et al. | 424/465 |
| 5,298,261 A | 3/1994 | Pebley et al. | 424/488 |
| 5,358,717 A | 10/1994 | Kuramoto et al. | 424/464 |
| 5,370,878 A | 12/1994 | Shah | 424/469 |
| 5,393,531 A | 2/1995 | Gerhard et al. | 424/466 |
| 5,424,075 A | 6/1995 | Daher et al. | 424/465 |
| 5,464,632 A | 11/1995 | Cousin et al. | 424/465 |
| 5,464,854 A | 11/1995 | dePadova | 514/381 |
| 5,501,861 A | 3/1996 | Makino et al. | 424/464 |
| 5,503,845 A | 4/1996 | Goede et al. | 424/464 |
| 5,527,543 A * | 6/1996 | Dopper et al. | 424/489 |
| 5,541,209 A | 7/1996 | Spinale | 514/381 |
| 5,622,985 A | 4/1997 | Olukuton et al. | 514/423 |
| 5,753,651 A | 5/1998 | dePodova | 514/223.5 |
| 5,994,348 A | 11/1999 | Ku et al. | 514/223.5 |

FOREIGN PATENT DOCUMENTS

| | | |
|---|---|---|
| EP | 475898 | 3/1992 |
| EP | 629408 | 12/1994 |
| EP | 708103 | 4/1996 |
| GB | 2270841 | 3/1994 |
| WO | 91/14679 | 10/1991 |

OTHER PUBLICATIONS

Desai et al., "Effect of formaldehyde formation on dissolution stability of hydrochlorothiazide bead formulations", *International Journal of Pharmaceutics*, 107 (2) 141–147 (1994).

Desai et al., "Effects of different types of lactose and disintegrant on dissolution stability of hydrochlorothiazide capsule formulations", *International Journal of Pharmaceutics*, 110, 257–265 (1994).

BASF, "Pluronic® & Tetronic® Surfactants," pp. 1–29 (1989).

I.R. Schmolka, "Poloxamers in the Pharmaceutical Industry", "Polymers For Controlled Drug Delivery", (ed. P. J. Tarcha) (1991) p. 189, 193, 197, 201, 205, 209 and 213.

Poloxamer, *Handbook of Pharmaceutical Excipients*, pp. 207–208 (1986).

Official Monographs, Poloxamer, USP23/NF18, pp. 2279–2281 (195).

Physicians' Desk Reference, World Search Report, Jan. 31,1994, "poloxamer", with attachments (the latter: formulations of Benylin DM, Cleocin Pediatric, Colace, Lariam, Peri–colace, Pediazole, Almay Eyelid, Baby Orajel and Geriplex–FS).

Lachman, L. et al., "The Theory and Practice of Industrial Pharmacy", Third Edition, (1986), cover page and p. 321.

Poloxamer, *Handbook of Pharmaceutical Excipients*, $2^{nd}$ Edition, pp. 352–354 (1995).

Povidone, *Handbook of Pharmaceutical Excipients*, $2^{nd}$ Edition, pp. 392, 396 and 399 (1995).

Desai et al., Int. J. Pharmaceutics, 142 (11), pp. 61–66 (1996).

* cited by examiner

*Primary Examiner*—Thurman K. Page
*Assistant Examiner*—Liliana Di Nola-Baron
(74) *Attorney, Agent, or Firm*—Michael D. Alexander

(57) ABSTRACT

Pharmaceutical compositions containing irbesartan, alone or in combination with a diuretic, providing tablets with a high relative amount of active agent and excellent wetting and disintegration properties.

13 Claims, No Drawings

PHARMACEUTICAL COMPOSITIONS CONTAINING IRBESARTAN

This application is a continuation of our prior copending application Ser. No. 09/390,868, filed Sep. 7, 1999 now abandoned, which in turn is a divisional of prior copending application Ser. No. 09/081,685, filed May 20, 1998, now U.S. Pat. No. 5,994,348, which in turn is a continuation of prior copending application Ser. No. 08/642,978, filed May 6, 1996, now abandoned, which in turn is a continuation-in-part of prior copending application Ser. No. 08/472,618, filed Jun. 7, 1995, now abandoned.

FIELD OF THE INVENTION

The present invention relates to pharmaceutical compositions containing irbesartan, preferably in the form of a tablet. The present invention also relates to tablets prepared from these compositions.

BACKGROUND OF THE INVENTION

Irbesartan, 2-n-butyl-4-spirocyclopentane-1-[(2'-(tetrazol-5-yl)biphenyl-4-yl)methyl]-2-imidazolin-5-one, is a potent, long-acting angiotensin II receptor antagonist which is particularly useful in the treatment of cardiovascular ailments such as hypertension and heart failure. Irbesartan has the following structure:

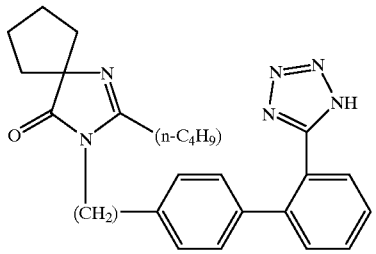

and is described in Bernhart et al., U.S. Pat. No. 5,270,317, incorporated herein by reference. Preferred pharmaceutical compositions of this drug contain, as active ingredient(s), irbesartan alone or in combination with a diuretic such as hydrochlorothiazide.

Irbesartan may be administered in dosages containing a substantial quantity of the active agent (e.g., 75–300 mg). Certain physical properties of the drug present a challenge in developing formulations suitable for preparing a tablet having both a substantial quantity of active agent and a small enough tablet mass to allow ease of swallowing.

Irbesartan is, for example, a fluffy material, with relatively low bulk and tap densities. These properties make it difficult to formulate a large amount of the drug into a small tablet with uniformity of weight, hardness, and other desirable tablet properties. In addition, irbesartan has certain undesirable flow characteristics, for example, is sticky and can adhere to surfaces such as tablet punch faces and dies, causing problems in tableting, especially on a high speed tablet press. The low aqueous solubility of irbesartan also presents a challenge, since, to keep the tablet mass small, only limited amounts of excipients may be added to facilitate wetting, disintegration, and ultimately, rapid and complete drug release. The addition of a diuretic such as hydrochlorothiazide, which is also a fluffy material exhibiting poor flow and low aqueous solubility, can further contribute to tableting problems.

Thus, there is a need in the art for pharmaceutical compositions containing irbesartan, alone or in combination with a diuretic, which have good properties for tablet formation, and yet which contain a low mass of excipients so that small, easily swallowed tablets with a high content of active agent may be prepared.

SUMMARY OF THE INVENTION

The present invention provides pharmaceutical compositions containing irbesartan, alone or in combination with a diuretic, which (1) have a minimal mass of added excipients, thereby allowing preparation of small, easily swallowed tablets which enhance patient acceptance and compliance, and yet which (2) have excellent properties for tablet formation, and (3) provide tablets with excellent wetting, disintegration, and ultimately, rapid and complete drug release properties.

In particular, the present invention provides pharmaceutical compositions, especially suitable for forming tablets, comprising from about 20 to about 70% by weight irbesartan or pharmaceutically acceptable salts thereof, and pharmaceutically acceptable excipients, wherein a tablet formed from aid composition has a dissolution performance such that about 80% or greater, preferably 85% or greater, of the irbesartan or salts thereof contained in said tablet dissolve within 30 minutes. The present compositions optionally also comprise from about 2 to about 33% diuretic, wherein the combined amount of irbesartan and diuretic does not exceed about 85%.

Preferred compositions containing irbesartan comprise, based on a total of 100% by weight: (a) from about 20 to about 70% (preferably, about 50%) irbesartan, (b) from about 1 to about 70% diluent, (c) from about 2 to about 20% binder, (d) from about 1 to about 10% disintegrant, (e) from about 0.1 to about 5% antiadherent, and (f) from about 0.2 to about 5% lubricant, and, optionally (g) from about 0.2 to about 6% surfactant, and/or (h) up to about 2% (preferably, from about 0.1 to about 1%) coloring agent.

Preferred compositions containing irbesartan and diuretic comprise, based on a total of 100% by weight: (a) from about 20 to about 70% (preferably, about 50%) irbesartan, (b) from about 2 to about 33% diuretic, wherein the combined loading of (a) and (b) does not exceed about 85%, (c) from about 1 to about 70% diluent, (d) from about 2 to about 20% binder, (e) from about 1 to about 10% disintegrant, (f) from about 0.1 to about 5% antiadherent, and (g) from about 0.2 to about 5% lubricant, and, optionally, (h) up to about 2% (preferably, from about 0.1 to about 1%) coloring agent.

The present compositions may contain up to about 70% w/w irbesartan, or up to about 85% w/w irbesartan and diuretic, and yet can be employed in the reproducible manufacture of tablets on a large scale. The present compositions can, for example, be compressed on high speed tableting equipment (especially, a high speed tablet press) to form tablets which are uniform in both weight and content and which exhibit desirable physical properties, including elegant appearance, low friability, and fast disintegration time. Tablets prepared from the present compositions are capable of releasing the active component(s), by dissolution, in a fast and reproducible manner.

Unless otherwise indicated, mention of irbesartan herein also includes pharmaceutically acceptable salts thereof.

DETAILED DESCRIPTION OF THE INVENTION

The present invention is described in further detail as follows. The components employed in the compositions of the present invention should be pharmaceutically acceptable, particularly as described in the National Formulary (NF) or United States Pharmacopeia (USP).

The "dissolution performance" of a tablet, as used herein with respect to irbesartan, refers to the weight % of irbesaftan, based on the total weight of irbesartan contained in the tablet, which dissolves within 30 minutes under the following conditions: using a tablet having a total weight of from 150 to 600 mg and a USP Apparatus 2, placing the tablet in 1000 mL of 0.1 N hydrochloric acid at 37° C., with a paddle speed of 50 rpm, and measuring the amount of irbesartan dissolved (especially, using UV at 244 nm or, when hydrochlorothiazide is also present, using HPLC, wavelength 272 nm) at 30 minutes. (If desired, the progress of dissolution may also be monitored at various time points.)

The "dissolution performance" of a tablet, as used herein with respect to a diuretic (preferably, hydrochlorothiazide), refers to the weight % of diuretic, based on the total weight of diuretic contained in the tablet, which dissolves within 30 minutes under the conditions described above for irbesartan dissolution. The dissolution performance for the diuretic preferably meets the USP dissolution specification for the diuretic (for hydrochlorothiazide, greater than 60% dissolution at 30 minutes). The dissolution performance of a tablet containing hydrochlorothiazide is most preferably such that about 90% or greater of the hydrochlorothiazide is dissolved at 30 minutes.

The "diuretic" employed in a composition of the present invention may be any suitable diuretic, or combination of two or more diuretics, such as hydrochlorothiazide, bendroflumethiazide, benzthiazide, chlorothiazide, chlorthalidone, cyclothiazide, hydroflumethiazide, methyclothiazide, metolazone, polythiazide, quinethazone, and trichlormethiazide. Preferably, the diuretic is hydrochlorothiazide.

The "diluent" employed in a composition of the present invention may be one or more compounds which are capable of providing bulk to obtain a desired tablet mass. It is desirable to employ the diluent in an amount at the lower end of the weight range for the diluent. Preferred diluents are inorganic phosphates such as dibasic calcium phosphate; sugars such as lactose hydrous or lactose anhydrous; and cellulose or cellulose derivatives such as microcrystalline cellulose.

The "binder" employed in a composition of the present invention may be one or more compounds which are capable of facilitating granulation of the irbesartan and/or diuretic into larger, denser, and/or more free-flowing particles. Preferred binders are alginic acid (most preferably employed in the range of 2–5% by weight) or sodium alginate (most preferably employed in the range of 2–3% by weight); cellulose or cellulose derivatives such as carboxymethylcellulose sodium (most preferably employed in the range of 2–6% by weight), ethylcellulose (most preferably employed in the range of 2–3% by weight), hydroxyethyl cellulose (most preferably employed in the range of 2–5% by weight), hydroxypropyl cellulose (most preferably employed in the range of 2–6% by weight), hydroxypropyl methylcellulose (most preferably employed in the range of 2–5% by weight), or methylcellulose (most preferably employed in the range of 2–6% by weight); gelatin (most preferably employed in the range of 2–10% by weight); povidone (polyvinylpyrrolidone, i.e., 1-ethenyl-2-pyrrolidinone homopolymer) (e.g., povidone K-30) (most preferably employed in the range of 2–20% by weight); or starch (most preferably employed in the range of 5–20% by weight) or pregelatinized starch (most preferably employed in the range of 2–20, such as 5–20% by weight).

The "disintegrant" employed in a composition of the present invention may be one or more compounds which are capable of facilitating the break up of a tablet prepared from the composition when placed in contact with an aqueous medium. Preferred disintegrants are alginic acid (most preferably employed in the range of 2–5% by weight) or sodium alginate (most preferably employed in the range of 2.5–10% by weight); cellulose or cellulose derivatives such as carboximethylcellulose sodium (most preferably employed in the range of 2–6% by weight), microcrystalline cellulose (most preferably employed in the range of $5^-$–15% by weight), powdered cellulose (most preferably employed in the range of 5–15% by weight), or croscarmellose sodium (cross-linked polymer of carboxymethylcellulose sodium) (most preferably employed in the range of 2–5% by weight); crospovidone (cross-linked homopolymer of N-vinyl-2-pyrrolidinone, i.e., cross-linked 1-ethenyl-2-pyrrolidinone) (most preferably employed in the range of 2–5% by weight); pregelatinized starch (most preferably employed in the range of 5–10% by weight), sodium starch glycolate (most preferably employed in the range of 2–8% by weight), or starch (most preferably employed in the range of 3–15% by weight).

The "antiadherent" employed in a composition of the present invention may be one or more compounds which are capable of reducing the stickiness of the formulation, for example, preventing adherence to metal surfaces. Preferred antiadherents are silicon-containing compounds such as silicon dioxide (most preferably employed in the range of 0.25–5% (such as 0.5–2 or 2.5 to 3.0%) by weight), magnesium trisilicate (most preferably employed in the range of 0.5–2% by weight), or talc (most preferably employed in the range of 1–5% by weight).

The "lubricant" employed in a composition of the present invention may be one or more compounds which are capable of preventing tableting problems, such as those relating to the release of a tablet prepared from the composition from the apparatus on which it is formed, for example, preventing adherence to the face of the upper punch (picking) or lower punch (sticking) of a tableting apparatus. Preferred lubricants are fatty acids or fatty acid derivatives such as calcium stearate (most preferably employed in the range of 0.5–2% by weight), glyceryl monostearate (most preferably employed in the range of 0.5–2% by weight), glyceryl palmitostearate (most preferably employed in the range of 0.5–2% by weight), magnesium stearate (most preferably employed in the range of 0.2–2% by weight), sodium lauryl sulfate (most preferably employed in the range of 1–2% by weight), sodium stearyl fumarate (most preferably employed in the range of 0.5–2% by weight), zinc stearate (most preferably employed in the range of 0.5–1.5% by weight).or stearic acid (most preferably employed in the range of 1–3% by weight); hydrogenated vegetable oil (most preferably employed in the range of 1–5% by weight); polyalkylene glycols such as polyethylene glycol (most preferably employed in the range of 1–5% by weight); sodium benzoate (most preferably employed in the range of 2–5% by weight); or talc (most preferably employed in the range of 1–5% by weight).

The "surfactant" employed in a composition of the present invention may be one or more compounds which are capable of improving the wetting of the tablets and/or enhancing dissolution. Preferred surfactants are sodium lauryl sulfate (most preferably employed in the range of 0.2–6% by weight), and poly(oxyethylene),poly (oxypropylene) block co-polymers such as poloxamers, especially poloxamer 188 (most preferably employed in the range of 1–6% by weight).

The "coloring agent" (or "colorant") employed in a composition of the present invention may be one or more compounds which impart a desired color to a tablet prepared from the composition. Addition of a coloring agent may be used, for example, so that tablets of different potencies may be easily distinguished. Preferred coloring agents are ferric oxides, which are universally accepted.

As can be seen from the above, a single compound may perform two or more functions. Calculation of weight percent is preferably on the basis of the primary function of a compound in a given composition. The present compositions preferably consist essentially of, most preferably, consist of the above-described components.

Preferred Composition

Preferred compositions of the present invention contain one or more of the following components in the indicated concentration range (% by weight): irbesartan, 20 to 60 (e.g., 25 to 60), such as 30 to 60, most preferably, 30 to 50, especially about 50%; diuretic, 2 to 20, most preferably 2 to 17, especially 4 to 9%; diluent, I to 70, most preferably 1 to 60, especially 1 to 40%; binder, 5 to 20, most preferably 5 to 15%; disintegrant, 4 to 8, most preferably about 5%; antiadherent, 0.25 to 5.0% (such as 0.25 to 1.5, most preferably 0.7 to 0.8%, for example, when a diuretic is present or 2.5 to 3.0%, for example, when a diuretic is not present); lubricant, 0.5 to 1.5, most preferably about 1%; and surfactant, 1 to 3, most preferably, about 3%.

The following tables recite preferred compositions of the present invention which produce tablets of especially high quality and superior performance. Table A recites preferred compositions containing irbesartan; Table B recites preferred compositions containing irbesartan in combination with a diuretic.

TABLE A

IRBESARTAN

| Preferred Ingredient | Component | Concentration Range (% w/w) |
|---|---|---|
| irbesartan | active drug | 20–50 |
| lactose hydrous | diluent | 1–70 |
| microcrystalline cellulose (e.g., Avicel ® PH 102+) | diluent | 5–20 |
| pregelatinized starch (e.g., Starch ® 1500+) | binder | 10–20 |
| croscarmellose sodium (e.g., Ac-Di-Sol ®+) | disintegrant | 4–8 |
| poloxamer,* especially poloxamer 188 (e.g., Pluronic ® F68+) | surfactant | 1–6 |
| silicon dioxide (e.g., Syloid ® 244+) | antiadherent | 0.25–5.0 (0.25 to 1.5 or, especially, 2.5 to 3.0) |
| magnesium stearate | lubricant | 0.5–1.5 |
| TOTAL | | 100 |

*Optional, but preferred, componet.
+These exemplary compounds may be used as desired throughout this specification as appropriate. For example, Starch ® 1500 may be used as desired wherever pregelatinized starch appears in this specification.

In the above compositions of Table A, the combination of magnesium stearate and silicon dioxide provides a superior lubrication effect while minimizing any decline in tablet dissolution performance; the intragranular:extragranular placement ratio of the disintegrant croscarmellose sodium is superior (e.g., 1:1); and the poloxamer surfactant improves the aqueous granulation of irbesartan (which is hydrophobic), eases the ejection of tablets after compression and accelerates the dissolution of the irbesartan active agent.

TABLE B

IRBESARTAN IN COMBINATION WITH DIURETIC

| Preferred Ingredient | Component | Concentration Range (% w/w) |
|---|---|---|
| irbesartan | active drug | 20–50 |
| hydrochlorothiazide | diuretic, active drug | 2–20* |
| lactose hydrous | diluent | 1–70 |
| microcrystalline cellulose (e.g., Avicel ® PH 102) | diluent | 10–20 |
| croscarmellose sodium (e.g., Ac-Di-Sol ®) | disintegrant | 4–6 |
| pregeletinized starch (e.g., Starch ® 1500) | binder | 10–20 |
| silicon dioxide (e.g., Syloid ® 244) | antiadherent | 0.5–1.0 |
| magnesium stearate | lubricant | 0.5–1.5 |
| TOTAL | | 100 |

*The concentration of hydrochlorothiazide can vary according to the hydrochlorothiazide potency sought in the combination tablet, which preferably ranges from 6.25 mg to 25 mg per tablet.

The compositions of Tables A and B preferably also contain 0.08 to 0.12% by weight ferric oxide, red and 0.08 to 0.12% by weight ferric oxide, yellow as a colorant.

Methods of Manufacture

Tablets may be prepared from the present compositions by any suitable method for forming tablets. Preferably, tablets are prepared from the present compositions by a wet granulation process. An exemplary such method comprises the following steps:

(a) preparing an intragranular composition by:
   (i) mixing the irbesartan, diuretic (for combined tablets), a portion of the diluent (preferably, from about 5 to about 80% by weight of the total diluent), a portion of the disintegrant (preferably, from about 50 to about 80% by weight of the total disintegrant), the binder, and, optionally, a portion of the antiadherent (preferably, from about 50 to about 80% by weight of the total antiadherent), to form a powder blend and, optionally, sizing the blend (e.g., milling the blend to break up aggregates);
   (ii) re-mixing the blend;
   (iii) granulating the blend with a granulating fluid, preferably water and/or an aqueous solution of the surfactant, to form granules (e.g., using a high shear mixer/granulator);
   (iv) drying the granules (e.g., in an oven or, preferably, in a fluid bed dryer); and
   (v) sizing the dried granules (e.g., by milling or screening);
(b) preparing a mixture of the sized granules of step (a)(v) with an extragranular composition by:
   (i) mixing the remainder of the diluent, the remainder of the disintegrant, the antiadherent or the remainder of the antiadherent, and, optionally, the coloring agent, where one or more of these may be pre-blended, sized (e.g., milled to break up aggregates) and re-mixed prior to this step, with the sized granules from step (a)(v) to form a granule blend; and
   (ii) mixing the lubricant with the granule blend; and
(c) compressing the mixture from step (b)(ii) to form tablets (for example, employing a tablet press).

The solid starting materials of the present compositions are preferably screened prior to use. The weight ratio of water (preferably, purified water, USP or water for injection, .USP) to solids employed in step (a)(iii) is preferably within the range of from about 0.25:1 to about 0.6:1.

The tablets may, optionally, be finished or coated such as by methods known in the art.

The tablets prepared from the compositions of the present invention preferably contain (per tablet) from about 25 to about 300 mg of irbesartan, most preferably from about 75 to 300 mg of irbesartan and, for the combined tablets, an additional amount of from about 1 to about 25 mg of diuretic, most preferably from about 6.25 to about 25 mg of hydrochlorothiazide. The total weight of the tablets prepared is preferably from about 50 to about 600 mg. In addition to tablets, the compositions of the present invention may be used to prepare beads, granules for dispersion or capsules, the latter, for example, filled with powder or the aforementioned beads or granules. Methods such as those well known in the art may be used to prepare these dosage forms.

The compositions and tablets of the present invention may be used to treat or prevent disorders such as those described in U.S. Pat. No. 5,270,317, incorporated herein by reference. Such disorders include cardiovascular disorders, for example, hypertension or heart failure, venous insufficiency, as well as glaucoma, diabetic retinopathy, renal insufficiency and various complaints of the central nervous system. The present compositions or tablets are preferably administered orally, in an effective amount, to a mammalian (especially, human) subject to treat or prevent the aforementioned disorders. For human subjects, preferred dosages of from about 75 mg to about 300 mg of irbesartan (alone or in combination with a diuretic) may be administered, for example, 1 to 2 times per day.

The following Examples are provided to illustrate preferred embodiments of the invention, and are not intended to limit the scope of the present claims.

EXAMPLE 1

Preparation of Tablets Containing Irbesartan

Tablets containing irbesartan were prepared in three potencies from the composition of the present invention described in the following Table 1: (1) 75 mg irbesartan with a total weight of 150 mg per 10 tablet; (2) 150 mg irbesartan with a total weight of 300 mg per tablet; and (3) 300 mg irbesartan with a total weight of 600 mg per tablet.

TABLE 1

| Ingredient | Component | Concentration (% w/w) |
|---|---|---|
| INTRAGRANULAR | | |
| irbesartan | active drug | 50 |
| lactose hydrous, NF | diluent | 10.25 |
| pregelatinized starch, NF | binder | 15.0 |
| croscarmellose sodium, NF | disintegrant | 2.5 |
| poloxamer 188, NF | surfactant | 3.0 |
| EXTRAGRANULAR | | |
| microcrystalline cellulose, NF | diluent | 15.0 |
| croscarmellose sodium, NF | disintegrant | 2.5 |
| silicon dioxide, NF | antiadherent | 0.75 |
| magnesium stearate, USP | lubricant | 1.0 |
| TOTAL | 100.00 | 100.00 |

Using the above formulation, the tablets were prepared by a wet granulation process as follows. In this process, the total amount of water employed (by weight) was up to 50% of the total solids weight.

The irbesartan, lactose, pregelatinized starch, and a portion (½) of the croscarmellose sodium were mixed in a mixer. The powder blend prepared was passed through sizing equipment (cone mill or oscillator), and mixed in a mixer. The poloxamer 188 was dissolved in water (purified, USP or water for injection, USP) (25% of the weight of total solids), and used to wet granulate (with the further addition of water in an amount which was up to 25% of the weight of total solids as needed) the mixed powder. The granules obtained were dried (tray or fluid bed dryer) until the loss-on-drying (LOD) was 2% or less. The dried granules were passed through a screen or milled to obtain the proper size (1 to 3 mm).

The sized granules were mixed with the silicon dioxide, the microcrystalline cellulose and the remaining croscarmellose sodium in a mixer. The blend obtained was then mixed with the magnesium stearate. By compressing the mixture using tableting equipment, tablets were prepared for each potency having the compositions indicated in the following Table 2.

TABLE 2

| Ingredient | 75 mg Potency (mg) | 150 mg Potency (mg) | 300 mg Potency (mg) |
|---|---|---|---|
| irbesartan | 75.00 | 150.00 | 300.00 |
| lactose hydrous, NF | 15.38 | 30.75 | 61.50 |
| microcrystalline cellulose, NF | 22.50 | 45.00 | 90.00 |
| pregelatinized starch, NF | 22.50 | 45.00 | 90.00 |
| croscarmellose sodium, NF | 7.50 | 15.00 | 30.00 |
| poloxamer 188, NF (or Pluronic F68, NF) | 4.50 | 9.00 | 18.00 |
| silicon dioxide, NF | 1.12 | 2.25 | 4.50 |
| magnesium stearate, USP | 1.50 | 3.00 | 6.00 |
| Tablet Weight | 150.00 | 300.00 | 600.00 |

EXAMPLE 2

Preparation of Tablets Containing Irbesartan: Alternative Formulation

Tablets were prepared having the composition of the following Table 3 by a method analogous to that of Example 1.

TABLE 3

| Ingredient | Amount mg/tablet (% w/w) |
|---|---|
| INTRAGRANULAR | |
| irbesartan | 300.0 (50) |
| lactose hydrous, NF (diluent) | 121.5 (20.25) |
| povidoneK-30, USP (binder) | 30.0 (5) |
| croscarmellose sodium (disintegrant) | 24.0 (4) |
| Pluronic F681 NF (poloxamer, surfactant) | 18.0 (3) |
| EXTRAGRANULAR | |
| microcrystalline cellulose, NF (diluent) | 90.0 (15) |
| croscarmellose sodium (disintegrant) | 6.0 (1) |
| silicon dioxide, NF (antiadherent) | 4.5 (0.75) |
| magnesium stearate | 6 (1) |

TABLE 3-continued

| Ingredient | Amount mg/tablet (% w/w) |
|---|---|
| (lubricant) | |
| TOTAL WEIGHT | 600.00 (100) |

EXAMPLE 3

Preparation of Combination Tablets: Irbesartan and Hydrochlorothiazide

Tablets containing a combination of irbesartan and hydrochlorothiazide were prepared in two potencies from the composition of the present invention described in the following Table 4: (1) 75 mg irbesartan/12.5 mg hydrochlorothiazide with a total weight of 150 mg per tablet; and (2) 150 mg irbesartan/12.5 mg hydrochlorothiazide with a total weight of 300 mg per tablet.

TABLE 4

| Ingredient | Amount (% w/w) in 75 mg/12.5 mg Tablets | Amount (% w/w) in 150 mg/12.5 mg Tablets |
|---|---|---|
| INTRAGRANULAR | | |
| irbesartan | 50.00 | 50.00 |
| hydrochlorothiazide, USP | 8.33 | 4.17 |
| lactose hydrous NF (diluent) | 4.72 | 8.88 |
| pregelatinized starch, NF (binder) | 15.00 | 15.00 |
| croscarmellose sodium, NF (disintegrant) | 4.00 | 4.00 |
| EXTRAGRANULAR | | |
| microcrystalline cellulose, NF (diluent) | 15.00 | 15.00 |
| croscarmellose sodium, NF (disintegrant) | 1.00 | 1.00 |
| silicon dioxide, NF (antiadherent) | 0.75 | 0.75 |
| ferric oxide, NF, red (colorant) | 0.10 | 0.10 |
| ferric oxide, NF, yellow (colorant) | 0.10 | 0.10 |
| magnesium stearate, NF (lubricant) | 1.00 | 1.00 |
| TOTAL | 100.00 | 100.00 |

Tablets having the above compositions were prepared using a wet granulation process as follows. The irbesartan and hydrochlorothiazide drug substances, the lactose hydrous, the pregelatinized starch, and a portion (⅘ of the total amount) of the croscarmellose sodium were weighed out and mixed. This powder blend was then milled to break up aggregates of the drug(s). The milled powder blend was then mixed again, followed by granulation with water (in an amount which was about 55% of the weight of total solids), in a mixer/granulator. The wet granules were then dried in drying equipment (tray or fluid bed dryer) until the LOD was 2% or less, followed by milling of the dried granules.

A color blend was made by mixing the ferric oxides with a portion (⅓ of the total amount) of the microcrystalline cellulose, milling the color blend, then mixing again. The remaining microcrystalline cellulose, the remaining croscarmellose sodium, the color blend, and the silicon dioxide were then weighed, screened, and mixed in a mixer with the dried, milled granules. In a final step, the magnesium stearate was weighed, screened and mixed with the above granule blend. This final blend was then compressed into tablets using a suitable tablet press.

Tablets Prepared

For the irbesartan/hydrochlorothiazide 75 mg/12.5 mg tablets, the tablet weight was 150 mg and the tablet hardness was 10–14 SCU (Strong Cobb Units). For the 150 mg/12.5 mg potency tablets, the tablet weight was 300 mg and the tablet hardness was 14–18 SCU. For both potency, tablets, the friability was less than 0.5%, the disintegration time was under 7 minutes, and the coefficient of variation for tablet weight was under 2%. In addition, the dissolution of these tablets meets the specification for irbesartan dissolution of 85% or greater in 30 minutes and easily meets the USP dissolution specification for hydrochlorothiazide of 60% in 30 minutes.

The tablets of this formulation were found to have good stability. Under certain conditions, hydrochlorothiazide can hydrolyze to form, as by-product products, a free amine degradant and formaldehyde (D.S. Desai et al., *International Journal of Phaxmaceutics*, 107(2), 141–47 (1994)). The selection of excipients can impact the stability of hydrochlorothiazide. The use of pregelatinized starch as a binder in the present compositions was found to impart greater stability to hydrochlorothiazide than, for example, povidone (which resulted in the formation of quantities of the free amine degradant). Poloxamer was also found to increase the degradation of hydrochlorothiazide, and therefore, while employed as a preferred component in compositions without hydrochlorothiazide, poloxamer is not a preferred component for the irbesartan/hydrochlorothiazide compositions of the present invention. The aforementioned preferred compositions of the present invention containing irbesartan and hydrochlorothiazide are thus further advantageous since the excipients employed therein minimize or eliminate hydrochlorothiazide degradation.

EXAMPLE 4

Preparation of Combination Tablets: Irbesartan and Hydrochlorothiazide: Alternative Formulations Tablets were prepared having the compositions 4(A), 4(B), 4(C) or 4(D) of the following Table 5 by methods analogous to those of Example 3.

TABLE 5

| Ingredient | 4 (A) mg per tablet (% w/w) | 4 (B) mg per tablet (% w/w) | 4 (C) mg per tablet (% w/w) | 4 (D) mg per tablet (% w/w) |
|---|---|---|---|---|
| INTRAGRANULAR | | | | |
| irbesartan (active drug) | 75.0 (50) | 75.0 (50) | 150.0 (50) | 150.0 (50) |
| hydrochlorothiazide (diuretic, active drug) | 12.5 (8.33) | 12.5 (8.33) | 12.5 (4.17) | 12.5 (4.17) |
| lactose hydrous, NF (diluent) | 2.575 (1.72) | 17.575 (11.72) | 17.65 (5.88) | 47.65 (15.88) |
| pregelatinized starch, NF (binder) | 22.5 (15) | — | 45.0 (15) | — |
| povidone K-30, USP (binder) | — | 7.5 (5) | — | 15.0 (5) |
| croscarmellose sodium (disintegrant) | 6.0 (4) | 6.0 (4) | 12.0 (4) | 12.0 (4) |
| Pluronic F68, NF (poloxamer, surfactant) | 4.5 (3) | 4.5 (3) | 9.0 (3) | 9.0 (3) |

TABLE 5-continued

| Ingredient | 4 (A) mg per tablet (% w/w) | 4 (B) mg per tablet (% w/w) | 4 (C) mg per tablet (% w/w) | 4 (D) mg per tablet (% w/w) |
|---|---|---|---|---|
| EXTRAGRANULAR | | | | |
| microcrystalline cellulose NF (diluent) | 22.5 (15) | 22.5 (15) | 45.0 (15) | 45.0 (15) |
| croscarmellose sodium (disintegrant) | 1.5 (1) | 1.5 (1) | 3.0 (1) | 3.0 (1) |
| ferric oxide, NF red (colorant) | 0.15 (0.1) | 0.15 (0.1) | 0.3 (0.1) | 0.3 (0.1) |
| ferric oxide, NF yellow (colorant) | 0.15 (0.1) | 0.15 (0.1) | 0.3 (0.1) | 0.3 (0.1) |
| silicon dioxide (antiadherent) | 1.125 (0.75) | 1.125 (0.75) | 2.25 (0.75) | 2.25 (0.75) |
| magnesium stearate (lubricant) | 1.5 (1) | 1.5 (1) | 3.0 (1) | 3.0 (1) |
| TOTAL WEIGHT | 150.00 (100) | 150.00 (100) | 300.0 (100) | 300.0 (100) |

EXAMPLE 5

Preparation of Tablets Containing Irbesartan

Tablets containing irbesartan were prepared in three potencies from the composition of the present invention described in the following Table 6: (1) 75 mg irbesartan with a total weight of 150 mg per tablet; (2) 150 mg irbesartan with a total weight of 300 mg per tablet; and (3) 300 mg irbesartan with a total weight of 600 mg per tablet.

TABLE 6

| Ingredient | Component | Concentration (% w/w) |
|---|---|---|
| INTRAGRANULAR | | |
| irbesartan | active drug | 50 |
| lactose hydrous, NF | diluent | 10.25 |
| pregelatinized starch, NF | binder | 15.0 |
| croscarmellose sodium, NF | disintegrant | 2.5 |
| poloxamer 188, NF | surfactant | 3.0 |
| silicon dioxide, NF | antiadherent | 2.0 |
| EXTRAGRANULAR | | |
| microcrystalline cellulose, NF | diluent | 13.0 |
| croscarmellose sodium, NF | disintegrant | 2.5 |
| silicon dioxide, NF | antiadherent | 0.75 |
| magnesium stearate, USP | lubricant | 1.0 |
| TOTAL | 100.00 | 100.00 |

Using the above formulation, the tablets were prepared by a wet granulation process as follows. In this process, the total amount of water employed (by weight) was up to 50% of the total solids weight.

The irbesartan, lactose, pregelatinized starch, a portion (½) of the croscarmellose sodium, and a portion (about 73%) of the silicon dioxide were mixed in a mixer. The powder blend prepared was passed through sizing equipment (cone mill or oscillator), and mixed in a mixer. The poloxamer 188 was dissolved in water (purified, USP or water for injection, USP) (25% of the weight of total solids), and used to wet granulate (with the further addition of water in an amount which was up to 25% of the weight of total solids as needed) the mixed powder. The granules obtained were dried (tray or fluid bed dryer) until the loss-on-drying (LOD) was 2% or less. The dried granules were passed through a screen or milled to obtain the proper size (1 to 3 mm).

The sized granules were mixed with the remaining silicon dioxide, the microcrystalline cellulose and the remaining croscarmellose sodium in a mixer. The blend obtained was then mixed with the magnesium stearate. By compressing the mixture using tableting equipment, tablets were prepared for each potency having the compositions indicated in the following Table 7.

TABLE 7

| Ingredient | 75 mg Potency (mg) | 150 mg Potency (mg) | 300 mg Potency (mg) |
|---|---|---|---|
| irbesartan | 75.00 | 150.00 | 300.00 |
| lactose hydrous, NF | 15.38 | 30.75 | 61.50 |
| microcrystalline cellulose, NF | 19.50 | 39.00 | 78.00 |
| pregelatinized starch, NF | 22.50 | 45.00 | 90.00 |
| croscarmellose sodium, NF | 7.50 | 15.00 | 30.00 |
| poloxamer 188, NF (or Pluronic F68, NF) | 4.50 | 9.00 | 18.00 |
| silicon dioxide, NF | 4.12 | 8.25 | 16.50 |
| magnesium stearate, USP | 1.50 | 3.00 | 6.00 |
| Tablet Weight | 150.00 | 300.00 | 600.00 |

Tablets comprising irbesartan or a pharmaceutically acceptable salt thereof, prepared (such as is described herein) by mixing an extragranular composition with granules comprising an antiadherent (preferably, silicon dioxide), may dissolve more rapidly and/or completely, and thus may exhibit an improved dissolution performance.

EXAMPLE 6

Preparation of Tablets Containing Irbesartan: Alternative Formulation

Tablets were prepared having the composition of the following Table 8 by a method analogous to that of Example 5.

TABLE 8

| Ingredient | Amount mg/tablet (% w/w) |
|---|---|
| INTRAGRANULAR | |
| irbesartan | 300.0 (50) |
| lactose hydrous, NF (diluent) | 121.5 (20.25) |
| povidone K-30, USP (binder) | 30.0 (5) |
| croscarmellose sodium (disintegrant) | 24.0 (4) |
| Pluronic F68, NF (poloxamer, surfactant) | 18.0 (3) |
| silicon dioxide, NF (antiadherent) | 12.0 (2) |
| EXTRAGRANULAR | |
| microcrystalline cellulose, NF (diluent) | 78.0 (13) |
| croscarmellose sodium (disintegrant) | 6.0 (1) |
| silicon dioxide, NF (antiadherent) | 4.5 (0.75) |
| magnesium stearate (lubricant) | 6 (1) |
| TOTAL WEIGHT | 600.00 (100) |

What is claimed is:

1. A pharmaceutical composition, wherein said composition comprises, based on weight: (a) from about 20 to about 70% irbesartan or a pharmaceutically acceptable salt thereof, (b) from about 1 to about 70% diluent, (c) from about 2 to about 20% binder, (d) from about 1 to about 10% disintegrant, (e) from about 0.1 to about 5% antiadherent, (f) from about 0.2 to about 5% lubricant, (g) from about 0.2 to about 6% surfactant, and optionally (h) up to about 2% coloring agent wherein said diluent is lactose hydrous and microcrystalline cellulose; said binder is pregelatinized starch or povidone; said disintegrant is croscarmellose sodium; said antiadherent is silicon dioxide; said lubricant is magnesium stearate; and said surfactant is poloxamer 188; and wherein a tablet formed from said composition has a dissolution performance such that about 80% or greater of the irbesartan or salt thereof contained in said tablet dissolves within 30 minutes.

2. The pharmaceutical composition of claim 1, wherein a tablet formed from said composition has a dissolution performance such that about 85% or greater of the irbesartan or salt thereof contained in said tablet dissolves within 30 minutes.

3. A pharmaceutical composition of claim 1 comprising, based on weight, about 20 to 50% irbesartan; about 1 to 70% diluent; about 10 to 20% binder; about 4 to 8% disintegrant; about 0.25 to 5.0% antiadherent; about 0.5 to 1.5% lubricant; and about 1 to 6% surfactant.

4. A pharmaceutical composition of claim 1, comprising, based on weight, about 50% irbesartan; about 10.25% lactose hydrous; about 15.0% pregelatinized starch; about 5.0% croscarmellose sodium; about 3.0% poloxamer 188; about 15% microcrystalline cellulose; about 0.75% silicon dioxide; and about 1.0% magnesium stearate.

5. A pharmaceutical composition of claim 1, comprising, based on weight, about 50% irbesartan; about 10.25% lactose hydrous; about 15.0% pregelatinized starch; about 5.0% croscarmellose sodium; about 3.0% poloxamer 188; about 13% microcrystalline cellulose; about 2.75% silicon dioxide; and about 1.0% magnesium stearate.

6. A pharmaceutical composition of claim 1, comprising, based on weight, about 50% irbesartan; about 20.25% lactose hydrous; about 5.0% povidone K-30; about 5.0% croscarmellose sodium; about 3.0% poloxamer; about 15% microcrystalline cellulose; about 0.75% silicon dioxide; and about 1.0% magnesium stearate.

7. A pharmaceutical composition of claim 1, comprising, based on weight, about 50% irbesartan; about 20.25% lactose hydrous; about 5.0% povidone K-30; about 5.0% croscarmellose sodium; about 3.0% poloxamer; about 13% microcrystalline cellulose; about 2.75% silicon dioxide; and about 1.0% magnesium stearate.

8. A tablet formed from the composition of claim 1.

9. A tablet formed from the composition of claim 4.

10. A tablet formed from the composition of claim 5.

11. A tablet formed from the composition of claim 6.

12. A tablet formed from the composition of claim 7.

13. A tablet of claim 8, wherein the total weight of said tablet is from about 50 to about 600 mg.

* * * * *